(12) United States Patent
Redding, Jr.

(10) Patent No.: US 7,440,798 B2
(45) Date of Patent: Oct. 21, 2008

(54) SUBSTANCE DELIVERY SYSTEM

(76) Inventor: Bruce K. Redding, Jr., One Kathryn La., Broomall, PA (US) 19008

( * ) Notice: Subject to any disclaimer, the term of this patent is extended or adjusted under 35 U.S.C. 154(b) by 717 days.

(21) Appl. No.: 10/848,519

(22) Filed: May 18, 2004

(65) Prior Publication Data

US 2005/0131359 A1 Jun. 16, 2005

(51) Int. Cl.
*A61N 1/30* (2006.01)
(52) U.S. Cl. .................................................. 604/20
(58) Field of Classification Search ............. 604/19–22, 604/66, 289, 290; 601/2, 17; 607/154
See application file for complete search history.

(56) References Cited

U.S. PATENT DOCUMENTS

| | | |
|---|---|---|
| 2,065,295 A | 12/1936 | Sullivan |
| 3,212,756 A | 10/1965 | Hutton |
| 4,373,527 A | 2/1983 | Fischell |
| 4,592,753 A | 6/1986 | Panoz |
| 4,657,543 A | 4/1987 | Langer et al. |
| 4,767,402 A | 8/1988 | Kost et al. |
| 4,780,212 A | 10/1988 | Kost et al. |
| 4,787,888 A | 11/1988 | Fox |
| 4,821,740 A | 4/1989 | Tachibana et al. |
| 4,878,892 A | 11/1989 | Sibalis et al. |
| 4,953,565 A | 9/1990 | Tachibana et al. |
| 4,999,819 A | 3/1991 | Newnham et al. |
| 5,007,438 A | 4/1991 | Tachibana et al. |
| 5,016,615 A | 5/1991 | Driller et al. |
| 5,115,805 A | 5/1992 | Bommannan et al. |
| 5,135,479 A | 8/1992 | Sibalis et al. |
| 5,171,215 A | 12/1992 | Flanagan |
| 5,231,975 A | 8/1993 | Bommannan et al. |
| 5,267,985 A | 12/1993 | Shimada et al. |
| 5,276,657 A | 1/1994 | Newnham et al. |
| 5,282,785 A | 2/1994 | Shapland et al. |
| 5,323,769 A | 6/1994 | Bommannan et al. |
| 5,328,452 A | 7/1994 | Sibalis |
| 5,405,614 A * | 4/1995 | D'Angelo et al. ........... 424/449 |
| 5,421,816 A | 6/1995 | Lipkovker |
| 5,445,611 A | 8/1995 | Eppstein et al. |
| 5,458,140 A | 10/1995 | Eppstein et al. |
| 5,538,503 A | 7/1996 | Henley |
| 5,582,586 A | 12/1996 | Tachibana et al. |
| 5,656,016 A | 8/1997 | Ogden |
| 5,658,247 A | 8/1997 | Henley |
| 5,947,921 A | 9/1999 | Johnson et al. |
| 5,954,675 A | 9/1999 | Dellagatta |
| 5,978,701 A | 11/1999 | Johnson et al. |
| 6,002,961 A | 12/1999 | Mitragotri et al. |
| 6,018,678 A | 1/2000 | Mitragotri et al. |
| 6,024,717 A * | 2/2000 | Ball et al. ...................... 604/22 |
| 6,030,374 A | 2/2000 | McDaniel |
| 6,041,253 A | 3/2000 | Kost et al. |
| 6,086,572 A | 7/2000 | Johnson et al. |

(Continued)

*Primary Examiner*—Manuel Mendez

(57) ABSTRACT

A system being suitable for being secured substantially adjacent to a surface of a subject so as to effect delivery of at least one substance through the surface and into the subject. The system includes at least one aperture for receiving at least one ultrasonic transmission. The at least one substance is releasably secured substantially adjacent to the at least one aperture. A sonic member is disposed with respect to the at least one aperture so as to communicate the at least one transmission to the at least one substance so as to effect the delivery of the at least one substance through the surface of the subject.

4 Claims, 8 Drawing Sheets

U.S. PATENT DOCUMENTS

| | | |
|---|---|---|
| 6,171,294 B1 | 1/2001 | Southam et al. |
| 6,175,763 B1 | 1/2001 | Sorenson et al. |
| 6,181,963 B1 | 1/2001 | Chin et al. |
| 6,190,315 B1 | 2/2001 | Kost et al. |
| 6,234,990 B1 * | 5/2001 | Rowe et al. .................. 604/22 |
| 6,322,532 B1 | 11/2001 | D'Sa et al. |
| 6,392,327 B1 | 5/2002 | Lewis et al. |
| 6,475,148 B1 | 11/2002 | Jackson et al. |
| 6,537,224 B2 | 3/2003 | Mauchamp et al. |
| 6,569,099 B1 | 5/2003 | Babaev |
| 6,614,143 B2 | 9/2003 | Zhang et al. |
| 6,663,554 B2 | 12/2003 | Babaev |
| 6,678,554 B1 | 1/2004 | Sun et al. |
| 6,692,456 B1 | 2/2004 | Eppstein et al. |
| 2001/0007666 A1 | 7/2001 | Hoffman et al. |
| 2002/0096973 A1 | 7/2002 | Zhang et al. |
| 2002/0156400 A1 | 10/2002 | Babaev |
| 2003/0147943 A1 | 8/2003 | Luo et al. |
| 2006/0015059 A1 | 1/2006 | Redding |

* cited by examiner

SUBSTANCE DELIVERY SYSTEM

RELATED APPLICATIONS

This application claims priority of each of: U.S. patent application Ser. No. 60/300,343, filed Jun. 22, 2001 and entitled "ULTRASONIC TRANSDUCER APPARATUS AND METHOD OF USE SUITABLE FOR ULTRASONIC DRUG DELIVERY VIA A SYSTEM WHICH IS PORTABLE AND WEARABLE BY A SUBJECT"; U.S. patent application Ser. No. 60/300,292, filed Jun. 22, 2001 and entitled "TRANSDERMAL PATCH FOR USE IN ULTRASONIC DRUG DELIVERY APPLICATIONS"; and, U.S. patent application Ser. No. 60/227,359, filed Aug. 24, 2000, entitled "TRANSDERMAL DRUG DELIVERY SYSTEM UTILIZING A WEARABLE, PORTABLE SONIC APPLICATOR", the entire disclosures of which are each respectively hereby incorporated by reference herein as if being set forth in their respective entireties.

FIELD OF THE INVENTION

The present invention relates generally to substance delivery systems, and particularly to patches being suitable for use with an ultrasonically enhanced substance delivery.

BACKGROUND OF THE INVENTION

Generally, transdermal drug delivery systems employ a medicated device or patch which is affixed to the skin of a patient. The patch allows a medicinal compound contained within the patch to be absorbed through the skin layers and into the patient's blood stream. Transdermal drug delivery reduces the pain associated with drug injections and intravenous drug administration, as well as the risk of infection associated with these techniques. Transdermal drug delivery also avoids gastrointestinal metabolism of administered drugs, reduces the elimination of drugs by the liver, and provides a sustained release of the administered drug. Transdermal drug delivery also enhances patient compliance with a drug regimen because of the relative ease of administration and the sustained release of the drug.

Many medicinal compounds are not suitable for administration via known transdermal drug delivery systems since they are absorbed with difficulty through the skin due to the molecular size of the drug or to other bioadhesion properties of the drug. In these cases, when transdermal drug delivery is attempted, the drug may be found pooling on the outer surface of the skin and not permeating through the skin into the blood stream. Once such example is insulin, which has been found difficult to administer by means of transdermal drug delivery.

Some of the most critically needed medications are currently administered either by injection or oral dosage forms, which can have several drawbacks. In particular, chemotherapeutic agents are administered in increased dosages because of their need to survive degradation in the gastrointestinal tract. Many critical treatments for AIDS require a cocktail of drugs taken orally in solid dosage forms, several times a day to be effective. These medications are not suitable for administration via known transdermal drug delivery system because of the extensive dosing requirement, as well as the inability of the drug molecule to remain stable in a transdermal form. Moreover, the unsuitability of many drugs for conventional transdermal transfer may be due to low bioabsorbance of the drug across the skin layers.

Generally, conventional transdermal drug delivery methods have been found suitable only for low molecular weight medications such as nitroglycerin for alleviating angina, nicotine for smoking cessation regimens, and estradiol for estrogen replacement in post-menopausal women. Larger molecular medications such as insulin (a polypeptide for the treatment of diabetes), erythropoietin (used to treat severe anemia) and gamma-interferon (used to boost the immune systems cancer fighting ability) are all compounds not normally effective when used with conventional transdermal drug delivery methods.

However, the use of energy, such as ultrasonic energy, may be used to enhance the transdermal delivery of certain drugs. While these terms "ultrasound"and "ultrasonic" as used herein have their ordinary meaning, at least one source has defined "ultrasound" as mechanical pressure waves with frequencies above 20 kHz, H. Lutz et al., Manual of Ultrasound 3-12 (1984). Ultrasound may be generated by vibrating a piezoelectric crystal or other electromechanical element by passing an alternating current through the material. The use of ultrasound to increase the permeability of the skin to drug molecules has been termed sonophoresis or phonophoresis.

Previously described methods for using ultrasound to enhance transdermal drug delivery required the use in a clinical ultrasonic delivery setting, such as a physician's office, hospital or clinic. Moreover, the time for delivery of measurable amounts into human skin using these methods ranged from 10 minutes to 24 hours. In this case, the use of ultrasound-transdermal drug delivery treatment may be actually less desirable from a patient administration standpoint than a simple injection. This method is undesirable because of the need for the patient to visit the clinical setting and to remain on a treatment table while the ultrasound treatment is used to deliver the drug.

While the use of certain ultrasonic frequencies for the enhancing delivery of certain drugs in certain applications is known, results in such applications have been largely disappointing. In many cases the drug delivery pathway utilized enabled initial quantities of a drug to permeate the skin, but as longer periods of ultrasound were applied to the same location on the skin the delivery rate dropped off or was reduced to zero.

The exposure to ultrasound has been either continuous or pulsed to reduce heating of biological membranes. The depth of penetration of ultrasonic energy into living soft tissue is inversely proportional to the frequency, thus high frequencies have been suggested to improve drug penetration through the skin by concentrating the effect in the outermost skin layer, the stratum corneum. Pharmaceutical agents under sonic transdermal delivery may require variable frequencies and intensities in order to deliver therapeutic quantities of drugs to patients. Variables such as fat content and mass of a particular patient's tissue, through which the drug will be delivered, may vary the frequency and intensity requirements to obtain an effective dosing regimen.

Portable programmable devices and methods for ultrasonically enhancing substance delivery through a surface of a subject have not been disclosed. Because of the inefficiencies and lack of safety of the previous ultrasonic methods, no useful device has been proposed for the transdermal delivery of drugs with an ultrasonic assist.

Little effort has in the past been focused upon the design of a transdermal patch suitable for ultrasonic drug transport. The use of an ultrasonic applicator or sonicator applied to skin tissue has conventionally been employed with a pool of a target drug laying under the tip of the transducer and laying upon the skin surface. This method of ultrasonic drug delivery is not believed to be feasible in a commercial application. Other examples in which the skin is pre-sonicated and then a patch is placed over the sonicated skin area employ a passive drug delivery based upon the concept of induced increased permeability as effected by the ultrasonic transmission. This also is commercially non-feasible because of the length of time needed to pre-sonicate the skin and other factors.

In view of the foregoing problems and/or deficiencies, the development of a device for safely enhancing the permeability of the skin for noninvasive drug delivery in a more rapid time frame would be a significant advancement in the art. It would be another significant advancement in the art to provide an ultrasonic programmable device and method that can be used with a drug-containing patch. In addition, patient mobility, coupled with sustained release of a broad range of drugs, until now, has remained an elusive goal of transdermal drug delivery devices. Thus, the design of a suitable transdermal patch to accommodate an active ultrasonic transdermal delivery method is helpful to achieving a commercial ultrasonic drug delivery device.

SUMMARY OF THE PRESENT INVENTION

A system being suitable for being secured substantially adjacent to a surface of a subject so as to effect delivery of at least one substance through the surface and into the subject including: at least one aperture for receiving at least one ultrasonic transmission, the at least one substance being releasably secured substantially adjacent to the at least one aperture; and, a sonic member disposed with respect to the at least one aperture so as to communicate the at least one transmission to the at least one substance so as to effect the delivery of the at least one substance through the surface of the subject.

BRIEF DESCRIPTION OF THE DRAWINGS

The present invention will be more readily understood in connection with the non-limiting, attached figures, wherein.

DESCRIPTION OF THE PREFERRED EMBODIMENTS

Figure 1:
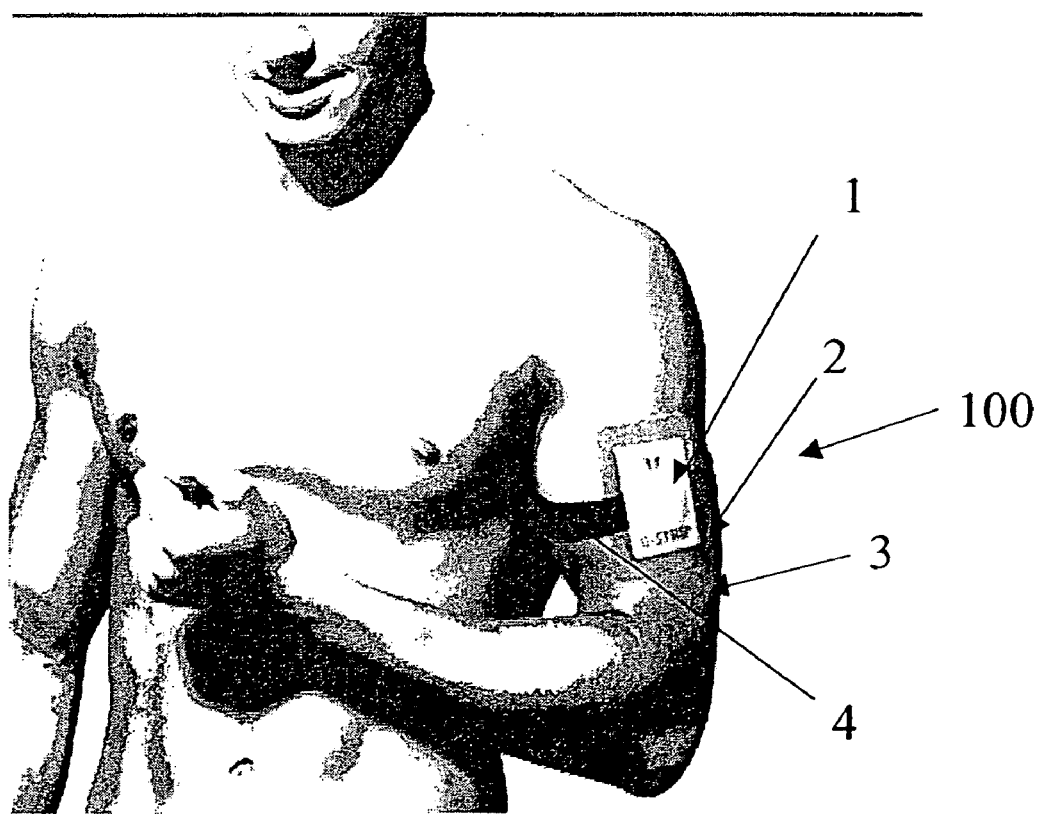
FIG. 1 is a transdermal patch with an ultrasonic generator, which is worn by the patient, as it is placed on the arm of a patient.

It is to be understood that the figures and descriptions of the present invention have been simplified to illustrate elements that are relevant for a clear understanding of the present invention, while eliminating, for purposes of clarity, many other elements found in substance delivery systems. Those of ordinary skill in the art will recognize that other elements are desirable and/or required in order to implement the present invention. However, because such elements are well known in the art, and because they do not facilitate a better understanding of the present invention, a discussion of such elements is not provided herein.

The present invention relates to patches, which may be employed with an ultrasonic drug delivery device, which is ideally worn by the patient.

According to an embodiment of the present invention, a transdermal patch is provided for enhancing transdermal drug delivery by the use of ultrasound. As used herein, the terms "drug" and "substance" may be used together or interchangeably and may include, but are not limited to, any substance including, but not limited to, a medicinal or non-medicinal substance which may be transported through a surface or membrane, including, but not limited to, tissue and other types of membranes. Use of ultrasonics is particularly effective in delivering larger pharmaceutically active compounds, wherein the transdermal patch is made to accommodate both the special needs of ultrasonic excitation through the patch construct and the delivery of medicinal compounds stored within the patch.

According to an embodiment of the present invention, a transdermal delivery device or patch is designed with materials to enable the transmission of ultrasound through the patch, effecting the delivery of medications stored within the patch, and to be used in conjunction with ultrasonic drug delivery processes. The transdermal patch may contain a substance, such as, for example, a particular medication or cocktail of medications for treatment of disease or relief of pain. A sonic applicator may be placed in the proximity of the patch, such as for example, over the top of the patch or into a pocket in the patch or may be contained within the patch construction itself. When the sonic applicator is activated by means of an external timing circuitry and driver mechanism or other suitable electronics, the sonic applicator generates an ultrasonic vibration or ultrasonic transmission through the transdermal patch. The effects of the energy of the ultrasonic signal, including, but not necessarily limited to, the vibration induced within the patient's skin, increase the absorption of the medication emanating from the transdermal patch through the skin into the patient's bloodstream.

According to an embodiment of the present invention, introduction of an ultrasonic signal to a transdermal patch increases the type of medications which can be employed in a transdermal delivery system, including large molecule medications, nutrient solutions, and proteins which heretofore were not capable of being delivered through a transdermal system.

According to an embodiment of the present invention, the use of an ultrasonic applicator with a transdermal patch provides full portability in the drug delivery system, as opposed to systems employing ultrasound to enhance drug delivery wherein the patient requires the assistance of a health professional, typically at a hospital, doctor's office or clinic.

According to an embodiment of the present invention, the system can be programmed to provide steady drug delivery or pulsed timed delivery at certain medication quantities, providing more flexibility and control over a particular patients dosing needs. Conventional transdermal drug delivery systems are generally steady state release devices providing a-one-size-fits-all regimen, which is not suited for all patient medication regimes.

According to an embodiment of the present invention, a transdermal patch may be employed with an ultrasonic drug delivery device which is ideally wearable by the patient, and/or is a programmable device using ultrasound for controlling transdermal and/or transmucosal flux rates of drugs and other molecules into the body.

According to an embodiment of the present invention, a method is provided for non-invasive delivery of molecules, including, but not necessarily limited to, biologically active molecules, through the skin or mucosal membranes using ultrasound and a transdermal patch.

According to an embodiment of the present invention, various ultrasound frequencies, intensities, amplitudes and/or phase modulations may be applied to control the magnitude of the transdermal flux from the patch to achieve a therapeutic or nutritional level.

According to an embodiment of the present invention, the design of the transdermal patch is such that the ultrasound energy is transmitted at a sufficiently high efficiency to permit drug permeation and contains an absorbent material, which holds the drug within the patch until liberated by ultrasound.

According to an embodiment of the present invention, a transducer or an array of transducers may be built into the patch. According to an aspect of the present invention, the transducers can be removably inserted into the patch.

According to an embodiment of the present invention, ultrasound may be combined with iontophoresis, electroporation, depilatories, and/or chemical enhancers such as surfactants to facilitate transdermal permeation. Other advantages and novel features of the invention will be evident from the description which follows, and in part will become apparent to those skilled in the art upon examination of the foregoing and/or the following.

FIG. 1 illustrates one embodiment of this transdermal drug (or other desirable substance) delivery system 100 of this invention. Transdermal drug delivery system 100 comprises an ultrasonic applicator 1, placed within functional proximity with a transdermal delivery device or patch 2. Patch 2, which contains the substance to be delivered, is placed in functional proximity to typically contact with the exterior of the patient's skin 3 by means of a strap or other suitable stabilizing device 4, which strap 4 holds the ultrasonic applicator 1 and patch 2 in desired proximity. Power for the ultrasonic applicator 1 is provided by power cells or other suitable power supply (not shown) which power supply is ideally rechargeable, and which may be located within strap 4 itself or other convenient location which provides for a fixed portable transdermal drug delivery system 100. For example, the power supply may be contained within the ultrasonic applicator device 1 itself or provided by an external source.

Reference is hereby made to commonly assigned and copending U.S. patent applications Ser. No. 10/946,863, entitled "ULTRASONICALLY ENHANCED SUBSTANCE DELIVERY METHOD", and Ser. No. 10/949,044, entitled "ULTRASONICALLY ENHANCED SUBSTANCE DELIVERY SYSTEM AND DEVICE", both filed on even date herewith, the entire disclosures of which are respectively hereby incorporated by reference herein.

FIG. 1 illustrates usage on the arm of the patient, according to an aspect of the present invention. Alternatively, the system may be placed in contact with some other part of the patient's body as determined by the medical personnel or other person administering the drug or other substance treatment regimen. Such locations may include, but are not necessarily limited to, the patient's chest (as in the case of nitroglycerin drug delivery, for example), abdomen, neck, back and legs.

Figure 2:
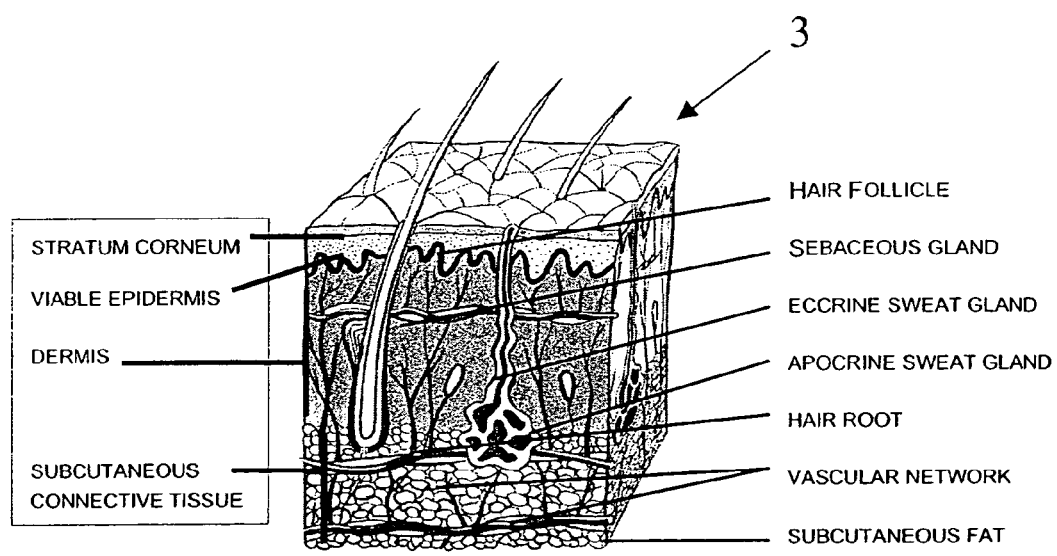
FIG. 2 is an illustration of the structure of human skin.

FIG. 2 illustrates the structure of human skin, showing the various structures comprising the skin. According to an aspect of the present invention, drug or other substance delivery may be accomplished by inducing a substance to travel down one or more hair follicles. In such an embodiment, the rate of delivery of a large molecule drug or other substance may be increased significantly, when such transmission is effected at the hair follicle of the skin. This effect may be achieved through the use of ultrasound, altered to a combination transmission incorporating both sawtooth and square waveforms. More specifically, in this embodiment, the pilosebaceous pores surrounding the hair follicle may become expanded with this method of substance delivery and a penetrating drug substance travels down the hair follicle to the hair root, whereupon it is absorbed into the blood stream located within the vascular network directly under the hair root. This substance pathway enables a greater quantity of the substance to be delivered ultrasonically than can be achieved simply by the use of cavitation effects upon the surface of the skin leading to microporation of the skin tissue or by simply enabling the drug to pool on the skin and travel through open skin pores.

In an embodiment, patch 2 may be subjected to ultrasound for the purpose of enhancing the penetration of substances, for example, medicinal compounds (drugs) contained within the patch, through tissue such as the skin or a mucous or other membrane, and into the patient's bloodstream. The ultrasonic drug delivery system 100 may be programmed to deliver a medicinal compound to the patient continuously (hereafter referred to as "sustained release") or intermittently (hereinafter referred to as "pulsed release"), whichever may be deemed more appropriate to a drug maintenance or other treatment regimen for a particular patient.

Figure 5:
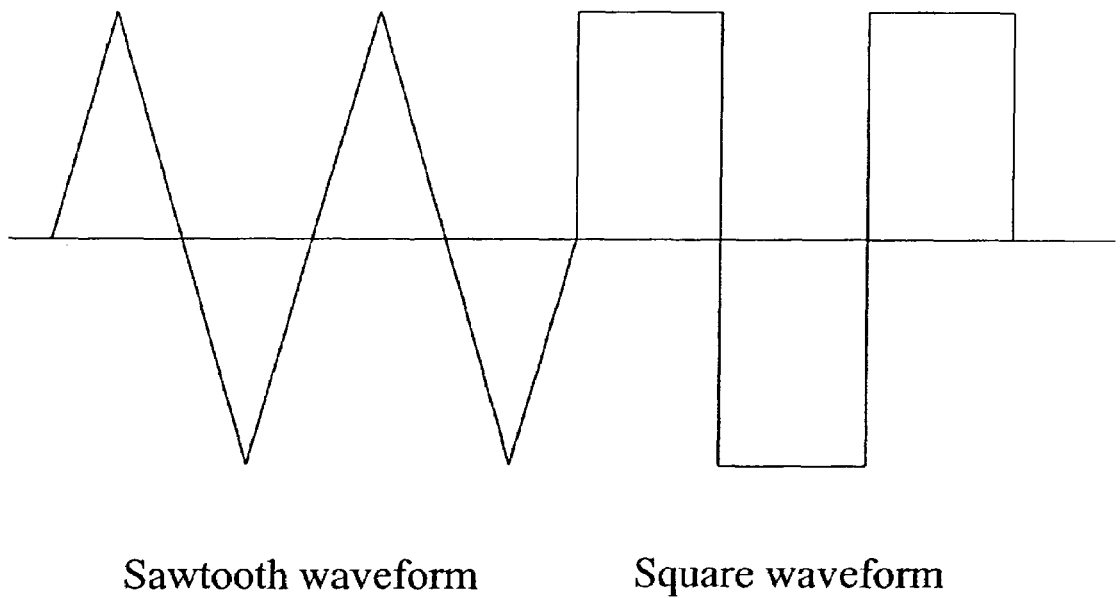
FIG. 5 illustrates an ultrasonic signal, which alternates from a sawtooth to a square waveform.

FIG. 5 illustrates one embodiment of an ultrasonic signal which generates the enhanced substance delivery of this invention. The signal of FIG. 5 employs a combination of a sawtooth and a square waveform. In this embodiment, the sawtooth wave front effects homogenization of the drug contained within the patch, and the square waveform which follows delivers ultrasonic energy to the surface of the skin to effect skin transport.

As referred to above, FIG. 2 generally illustrates the typical structure of human skin. Examples of pathways through the skin into the bloodstream include:
1. Breaching the Stratum Corneum.
2. Passing a pharmaceutical agent through sweat pores in the skin.
3. Passing a pharmaceutical agent through the skin by following the pilosebaceous pore to the hair root, and from there into the vascular network located at the base of the hair root.

In an embodiment of the invention, transdermal drug delivery may be achieved by utilizing drug pathways associated with the sweat pore and the hair follicle system on the patient's skin. In an embodiment, the ultrasonic frequency, intensity level and waveform dynamics may be adjusted to maximize drug delivery through the hair follicle pathway primarily and through the sweat pores in the skin surface secondarily, but not necessarily directly through the stratum corneum. It is believed that the amount of energy needed for piercing the stratum corneum is excessive and is also damaging to the fatty tissue. This transport through the patch and through the skin hair follicles and sweat pores in the embodiment of the invention may be enhanced by employing either or both of the following forces which may be exerted upon the skin surface:
1. First, in an embodiment, application of compression or tensile force to the surface of the skin may constrict the skin to allow the drug pathways to become more pronounced. Referring to FIG. 1 it can be seen that a strap holds the device to a patient's arm. In addition to securing the device to the patient's body, the strap also exerts a pressure upon the surface of the skin, constricting the skin. It is believed that the constriction offered by a tight strap may affect the permeability of the skin by: 1) exerting downward pressure upon the skin, perpendicular to the skin surface, 2) stretching the skin such that skin pores, such as the sweat pores and/or pilosebaceous pores, are more readily accessible to a drug; and/or 3) altering the location of the fat or other tissue underlying the outer skin layers such that transdermal delivery is enhanced, thus providing a more substantial pathway for drug delivery than was available by methods of the previous art which employed excessive cavitation energies to the skin surface in hope of breaching the stratum corneum.

Figure 3:
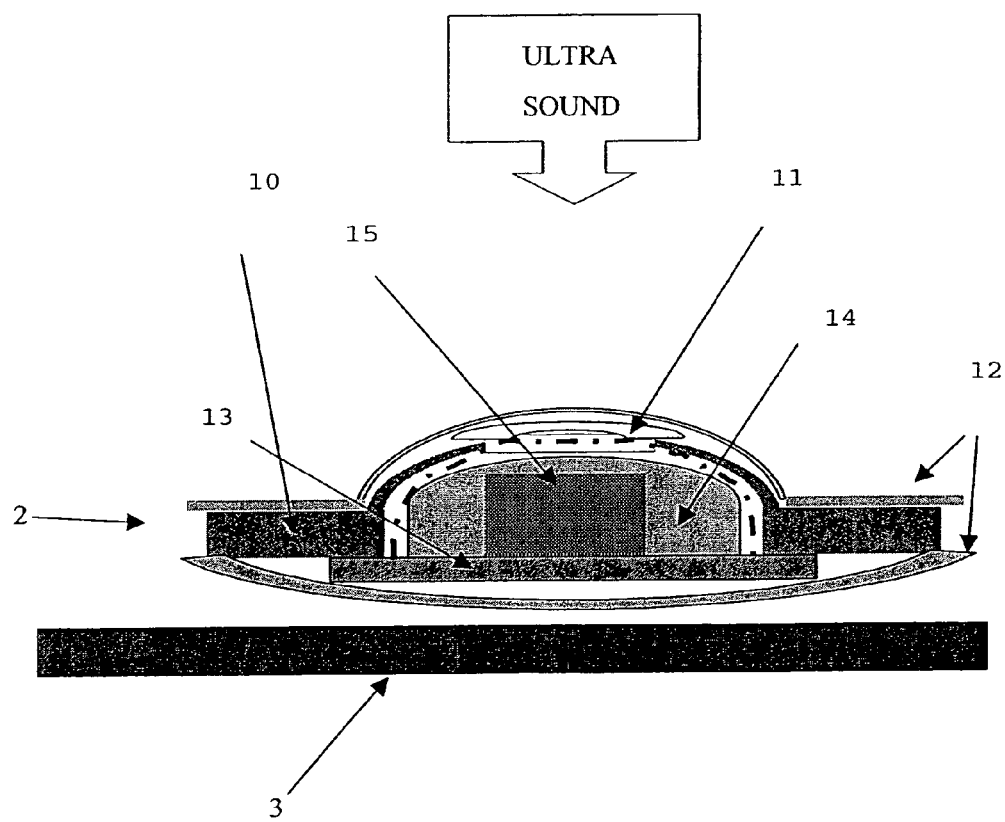
FIG. 3 illustrates for a transdermal patch wherein transducers are exterior to the patch.
Figure 4:
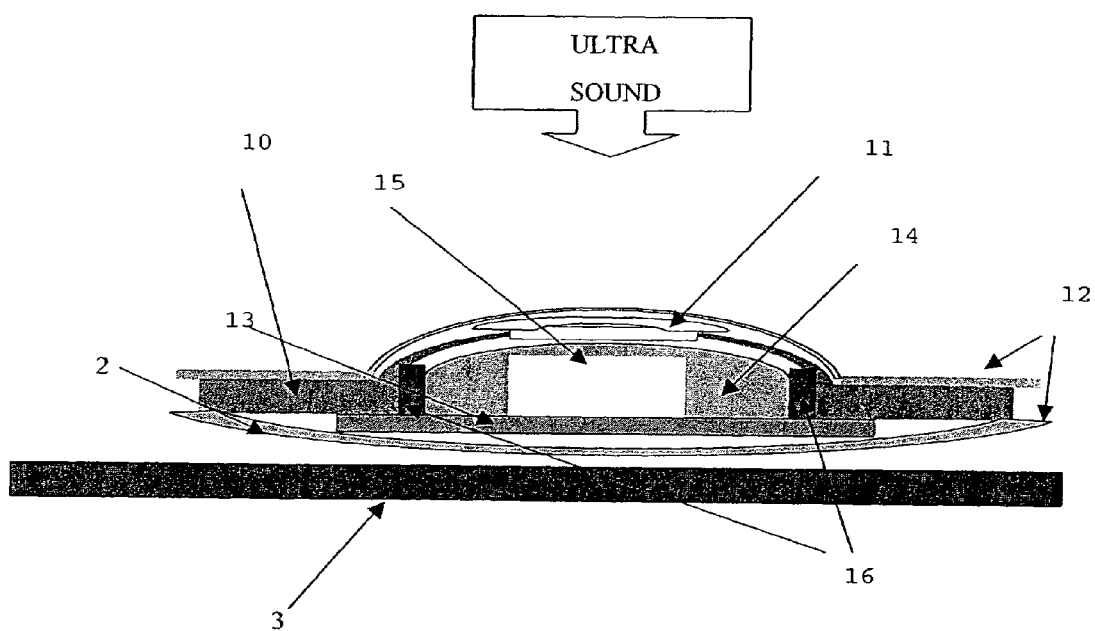
FIG. 4 illustrates a transdermal patch wherein the patch is constructed employing a gasket or sealer around the edges of the patch.

2. Second, application of force on skin which force is the pressure generated by an ultrasonic signal. It is believed that through the use of alternating waveforms the amount of energy transmitted to the surface of the skin can be minimized, while also providing a pressure wave effect upon the skin, enhancing drug delivery through the hair follicle and sweat pore system. Referring to FIG. 5, an embodiment employs a waveform, which alternates from sawtooth to square wave. The amplitude of and intensity of the wave shaping is believed to aid in both the homogenization of the drug contained within the transdermal patch (as seen in FIGS. 3 and 4), helping to miniaturize the beadlet size of the active pharmaceutical substance within the patch, and in drug transport through the skin. It is believed that the short, peaked portion of the ultrasonic waveform in a sawtooth shape helps with drug homogenization, without imparting destructive frequencies and cavitation to the drug substance. Upon conversion to the square waveform the ultrasonic transmission acts to massage and open the fatty tissue surrounding the hair follicles and sweat pores. Drugs permeating from the transdermal patch are in monomer form and/or reduced in droplet size, making them more suitable in dimension to pass through the skin. In an embodiment, the droplet size may be reduced to below approximately 50 Angstroms. The square waveform helps to "push" the drug through the pores and alongside the hair follicles, where the drug makes it way to the hair root, and directly into the bloodstream through the vascular network.

The parameters of ultrasound that can be changed to improve or control penetration include, but are not necessarily limited to: (1) frequency, (2) intensity, (3) time of exposure and/or (4) ultrasonic waveform. All of these parameters may be modulated simultaneously in a complex fashion to increase the effect or efficiency of the ultrasound as it relates to enhancing the transdermal molecular flux rate either into or out of the human body.

Since ultrasound is rapidly attenuated in air, a coupling agent, for example one having lowest realizable absorption coefficient that is non-staining, non-irritating, and slow drying, may be used to efficiently transfer the ultrasonic energy from the ultrasound transducer into the skin. When a chemical enhancer fluid or anti-irritant or both are employed, they may function as the coupling agent. For example, glycerin used as an anti-irritant may also function as a coupling agent. If needed, additional components may be added to the enhancer fluid to increase the efficiency of ultrasonic transduction. In an aspect of the present invention, resonance responsive gels may be used to further enhance the transport of drugs through the skin. In addition, maintaining the drug in a sterile and non-degradable form may be used to increase bioactivity.

In an embodiment of this invention, transdermal patch 2 may operate in conjunction with sonic applicator 1 to achieve ultrasonically promoted transdermal delivery of a desired substance. In particular, the contact between applicator 1 and patch 2 may be adjusted to insure efficient energy transmission. The materials used to construct the patch may be selected to maintain the intensity and power output of the ultrasonic transmission from the transducers through the transdermal patch. The present invention is particularly suited to deliver large molecule substances. For example, insulin has a large molecular size, and forms hexamers generally over 50 Angstroms, making it difficult to permeate through the pores of the skin. Insulin molecules tend to agglomerate when stored. Insulin therefore stored within a pocket of the patch may tend to agglomerate into even larger drug clump sizes, reducing skin transport potential.

To help alleviate this problem and to keep the drug at a size sufficiently small enough for skin transport, the waveform of the ultrasonic signal delivered by applicator 1 may be altered from time to time, using a sawtooth to a square waveform. FIG. 5 illustrates the alternating waveform concept wherein a sawtooth waveform is more efficient at homogenization of a drug within the patch, leading to increased skin transport as the ultrasonic waveform switches to a square wave shape. Under the sawtooth waveform the short period leads to high energy, with short duration of pressure amplitude, leading to a vibration effect with the targeted pharmaceutical substance. This vibration is with low heat and has the effect of mixing or homogenizing the drug within the patch. Smaller beadlet sizes are made possible by the sawtooth waveform.

Referring now to FIGS. 3 and 5, when the sonic transmission converts to square waveform induced, more energy is released through the patch, forcing the homogenized drug through the semi-permeable membrane 13 which may be made part of the patch secured to the surface of the skin. There the intensity of the sonic transmission acts upon the pores directly alongside the hair follicles as shown in FIG. 2 The square waveform enables the pores directly alongside the hair follicle to "open" and become more receptive to drug transport The deposited drug follows the hair follicle down through the epidermis to the base root of the follicle and is deposited directly into the blood stream within the skin's vascular network. From there the deposited drug is circulated through the body.

Referring now to FIG. 1, it can be seen a transdermal patch 2, is first placed within functional proximity, such as for example, in contact with skin 3 of the patient. In one embodiment of the invention, patch 2 may be affixed to skin 3 by adhesive or other appropriate means. Sonic applicator 1 may be placed in functional proximity to patch 2, such as, for example, in contact with patch 2, such that applicator 1 generates an energy signal, for example, an ultrasonic signal which signal transverses transdermal patch 2 underneath sonic applicator 1. The substance contained within transdermal patch 2 may be homogenized into smaller droplet sizes, which may tend to more readily diffuse the substance into and through the skin. The ultrasonic signal may also affect the skin lipids by disrupting and/or disorganizing them to permit the substance to be delivered. Alternatively, the hair follicle channels may serve as substance delivery channels. Regardless of the mechanism, the substance under the influence of ultrasonic signals penetrates the surface of the skin, travels through the various layers of the skin and fatty tissue and finally is absorbed into the bloodstream and/or tissue of the patient.

FIG. 3 illustrates an embodiment of the transdermal patch 2 of the present invention, referred to here as "patch A". Transdermal patch 2 is constructed with a backbone or backing material 10 into which a section, or aperture, has been created incorporating a sonic membrane 11 at the top of the patch 2. A peel-away film 12 seals patch 2 until use. Peel-away film 12 may be constructed by any suitable material, including, but not limited to, UV-resistant, anti-static polyethylene film (50 micrometer thickness) available from Crystal-X Corp., Sharon Hill, Pa. At the bottom of patch 2 is a semi-permeable member, such as a membrane or film, 13, which comes into functional proximity with the skin, such as within direct contact with the skin when in use. In the interior of patch 2 an absorbent pad 14 holds the desired drug or medication compound 15. Ultrasonic signals are transmitted through sonic membrane 11 and pass through the patch 2 by first traveling through the absorbent pad 14. Drug or other substance 15, is contained within the absorbent pad 14 until it is released by the ultrasonic signal, or by other means. The substance then passes through semi-permeable membrane 13 and is deposited on or through the surface of the patient's skin.

FIG. 4 illustrates yet another embodiment of transdermal patch 2 of the present invention referred to here as "patch B". Gasket 16 is placed between backbone 10 and absorbent pad 14. Gasket 16 may be composed of any suitable material, such as, for example, synthetic rubber. Gasket 16 forms a reservoir or well over which absorbent pad 14 is placed. When pressed upon the skin gasket 16 forms a barrier, which tends to restrict moisture and air from traveling under the patch and interfering with the ultrasonic signal intensity. Alternatively, a sealant compound, ultrasonic gel or other suitable material may be used for or in place of the gasket 16 to provide a sealing action around the borders of patch 2 to provide moisture protection, prevent leakage of substance or the drug from the patch and prevent air from entering under the patch.

Figure 6:
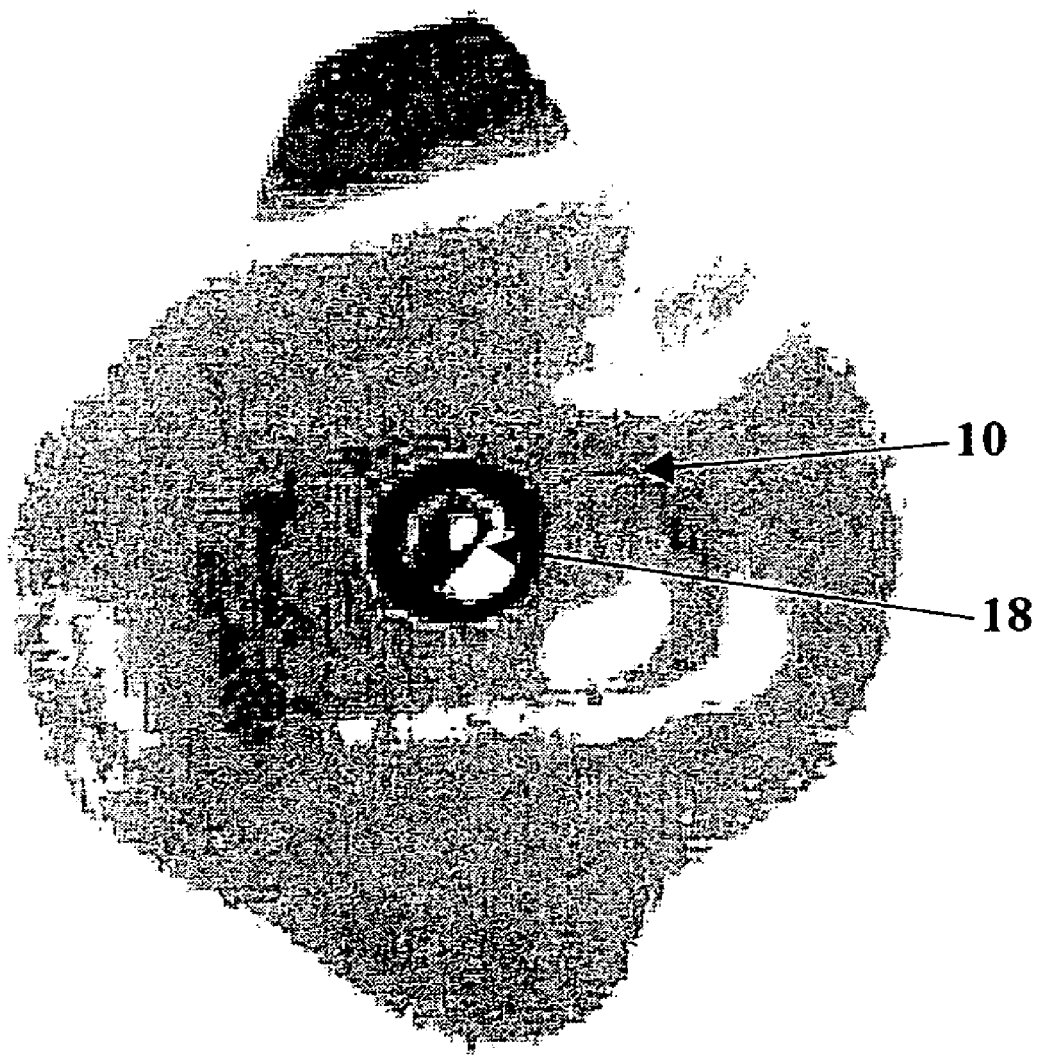
FIG. 6 illustrates a transdermal patch wherein a transducer or array of transducers is directly imbedded within the patch.

Referring now to FIG. 6, transducers 18 may be incorporated directly within patch 2 or in any other suitable location. In such construction a single transducer may be employed or an array of ultrasonic transducers may be desired.

Figure 7:
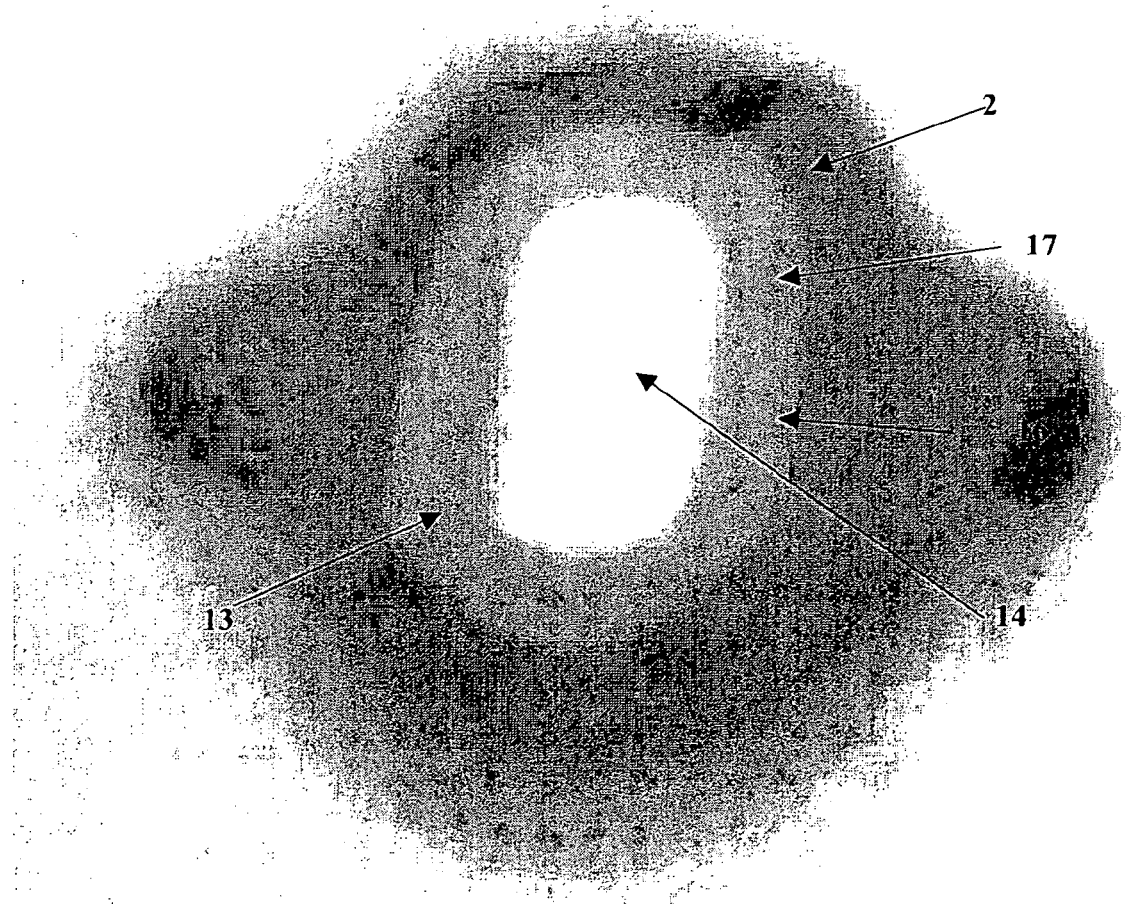
FIG. 7 illustrates a transdermal patch wherein a semipermeable film placed on the underside of the patch acts to provide a valving function with the administration of transmitted ultrasound though the patch.

FIG. 7 illustrates the underside of patch 2 showing well 17 together with semi-permeable membrane 13 over absorbent pad 14. Alternatively or in addition, sealing gasket or compound 16 may be placed in well 17 of the underside of patch 2.

Figure 8:
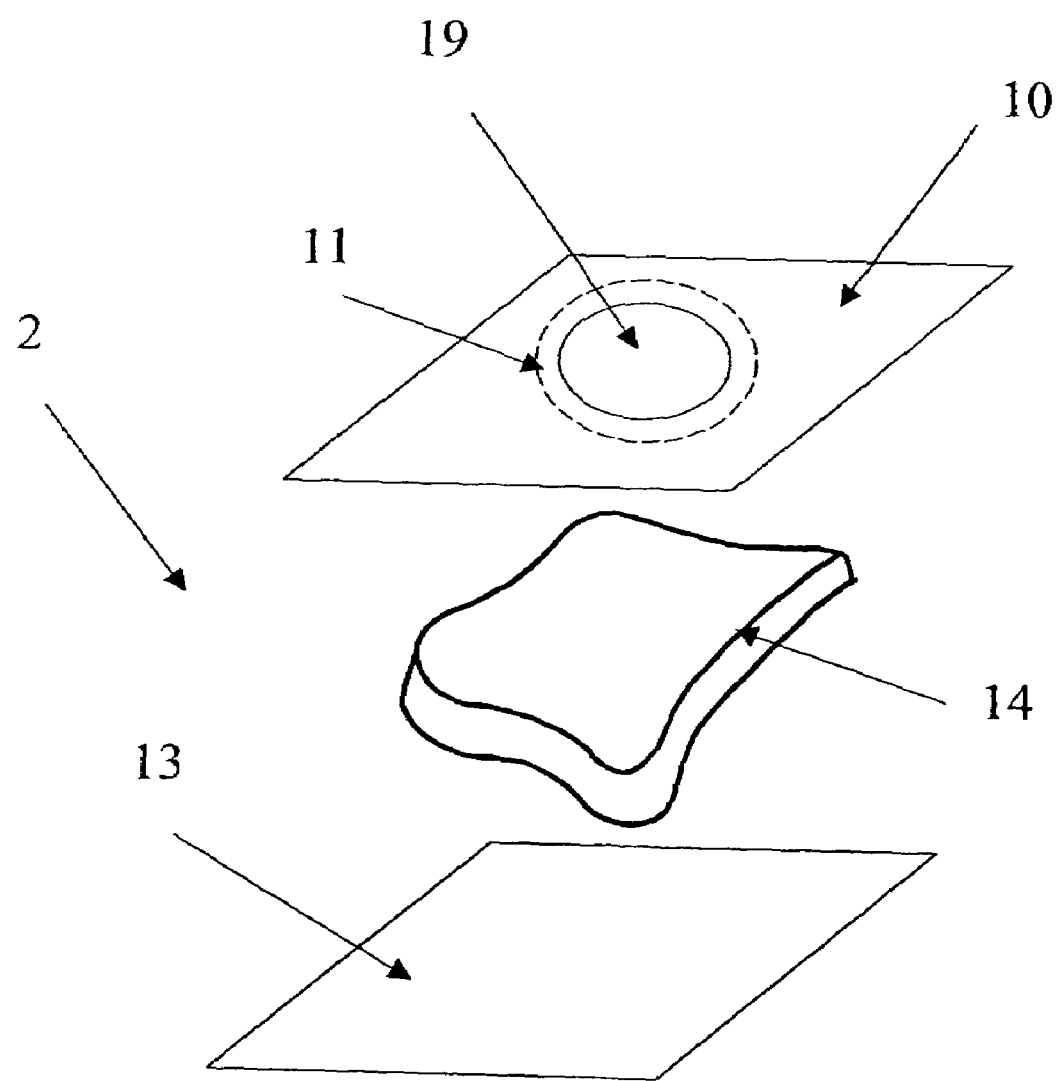
FIG. 8 illustrates a patch according to an embodiment of the present invention.

Referring now to FIG. 8, according to an embodiment of the present invention, a patch, or system, 2 being suitable for being secured substantially adjacent to a surface of a subject so as to effect delivery of at least one substance through the surface and into the subject is provided. The system 2 may include a backing layer, backing material, backbone, or backbone material, 10 and at least one aperture 19 formed in the backing layer 10 for receiving at least one ultrasonic transmission. The system 2 may further include a pad, such as an absorbent pad, 14 releasably securing the at least one substance substantially adjacent to the at least one aperture 19. A sonic member, such as a sonic membrane or film, 11 may be disposed with respect to the at least one aperture 19 so as to communicate the at least one transmission to the at least one substance so as to effect said delivery of the at least one substance through the surface of the subject. Optionally, a semi-permeable member, such as a membrane or film, or valving layer, 13 may be provided.

In an embodiment of the present invention, ultrasonic signals are transmitted using a combination frequency of a saw tooth and square waveforms as depicted in FIG. 5, which is believed to first homogenize substance 15 within the patch 2 and then to effect skin transport once the substance 15 has been deposited onto or through the surface of the skin. It may not be necessary for a coupling agent to be used between the skin and the semi-permeable membrane.

Referring again to FIGS. 3 and 4, sonic membrane 11 may be constructed of any suitable resonance compatible material which will enable the sonic transmission emanating from transducer(s) 18 to pass through sonic membrane 11, and then the absorbent pad 14 and thereafter through patch 2 and onto and/or through the patient's skin. Sonic membrane 11 may be composed of any suitable resonance compatible material which will conduct the ultrasonic transmission without unduly decreasing the effect generated by the transmission of frequency or intensity potential. Suitable resonance compatible materials used for sonic membrane 11 may include, without limitation, polyvinylidene chloride plastic film, such as, for example, the film sold as Saran®, including, but not necessarily limited to, Model Numbers Dow BLF-2014, Dow BLF-2015, Dow BLF-2023, Dow BLF-2050, Dow BLF-2052, Dow BLF-2057, and Dow BLF-2080, available from Dow Chemical Company, Midland, Mich.; and polyester film, for example, Mylar® film, including, but not necessarily limited to, Model Numbers M30, M33, M34, D887, MC2, and SBL-300, available from DuPont Teijin Films Div., Wilmington, Del. Polyvinylidene chloride film has been found to be effective as a sonic membrane material, however many other materials may also provide a similar function. The materials of patch 2 may be chosen or fabricated for resonance compatibility with a desired frequency and intensity of ultrasound to be used for a particular substances or drug's skin transport dynamics.

In an embodiment of the invention, sonic membrane 11 may be affixed to absorbent pad 14 with a suitable resonance compatible material, including, but not limited to, a flat layer of polymer epoxy. One suitable material is a polyurethane material, such as Uralite®, available from H. B. Fuller Company, St. Paul, Minn.

Absorbent pad 14 may be composed of any suitable material, such as a non-woven cellulose fiber or any similarly acting material which will absorb or otherwise hold drug 15 during storage within patch 2, but also release drug 15 upon transmission of the ultrasonic signal through patch 2. Other possible materials may be used, including, but not limited to, natural sponges, fused silica, and various woven and non-woven materials. Examples of suitable materials include, without limitation, CoTran 9729, a non-woven polypropylene material available from 3M, St. Paul, Minn.; Pop-Up Compressed Sponge (comprising 76% cellulose, 7.7% polyol, and 15.5% NaCl), available from Clipper Mill, San Francisco, Calif.; Microdon Web, Model Number M-261420025, a non-woven polyester fiber blend, available from 3M, St. Paul, Minn.; Vizorb #3010, a cellulose pad comprising wood pulp and ethylene vinyl acetate based synthetic latex, available from Buckeye Absorbent Products, Memphis, Tenn.; and Vicell #6009, a cellulose pad comprising wood pulp and ethylene vinyl acetate based synthetic latex, available from Buckeye Absorbent Products, Memphis, Tenn.

A semi-permeable membrane 13 may be placed at the bottom of patch 2, such that it comes into direct contact with the patient's skin. Such a semi-permeable membrane 13 may function like a valve, enabling drug 15 released from absorbent pad 14 to pass through semi-permeable membrane 13 only with the active generation of ultrasound. When no ultrasonic signal is present, semi-permeable membrane 13 prevents a significant amount of the drug from permeating the membrane onto or through the surface of the patient's skin. The valving action of semi-permeable membrane 13 may provide a means of controlling the dose delivered to the patient. It is believed that a sonicated skin section may remain permeable to a delivered substance such as a drug, for some amount of time after the ultrasonic signal has been terminated. If drug 15 were to reach the skin in this case, the skin might continue to absorb the drug even after the cessation of the ultrasonic signal. Assuming that a steady rate of delivery can be achieved with an active ultrasonic signal, the delivery of the proper dose would be proportional to the number of seconds or minutes that an active ultrasonic signal was present upon the skin surface. In such a manner the delivered drug dose levels would be comparable to the timing of active ultrasonic signal.

If continued skin permeation follows the cessation of active ultrasonic signal, it may be difficult to ascertain the exact amount of dose actually delivered to the patient. Hence a valving patch, which effectively shuts down drug delivery when the ultrasonic signal is terminated, may be provided. A sonically reactive semi-permeable membrane 13 may be used at the base of patch 2 in order to insure that patch 2 delivers the drug only with the presence of a ultrasonic signal, timed to deliver the proper dose by a timing circuit in sonic applicator device 1 depicted in FIG. 1, for example.

Suitable elastomeric materials that change properties when exposed to changes in pressure and/or temperature may be used to construct semi-permeable membrane 13. In an embodiment of the invention, any suitable material, including, but not limited to, natural sponge and perforated polymer films may be used as a semi-permeable membrane 13. Ultrasonic signals are believed to generate a cavitation effect in polymer films, expanding the diameter of the perforations of the film, thereby enabling the film to become more permeable. When an ultrasonic signal is not present, the elasticity of the film may enable it to return to its original structure and reduce the diameter of any perforation, thereby blocking a large molecule substance contained within patch 2 from further transport from patch 2 to the skin.

According to an embodiment of the invention, semi-permeable membrane 13 may be constructed of any suitable semi-permeable material that, in the absence of an ultrasonic signal, does not permit diffusion of a solution containing a drug across the membrane, but permits diffusion of a drug solution through the membrane upon being subjected to an ultrasonic signal.

According to an embodiment of the invention, semi-permeable membrane 13 may be constructed of any suitable thermoplastic material. Such a material may change properties upon being subjected to an increase in temperature as a result of a ultrasonic vibrations, and return to its original state upon cessation of the ultrasonic signal. According to an embodiment of the invention, semi-permeable membrane 13 may be constructed of any suitable thermoplastic elastomer that changes its permeability properties upon being subjected to an ultrasonic signal, allowing movement of the drug across the membrane, and substantially returns to its original permeability state upon cessation of the ultrasonic signal.

According to an embodiment of the invention, semi-permeable membrane 13 may be constructed of any suitable ionomer (ion-containing polymer), including, but not necessarily limited to, those ionomers that function as thermoplastic elastomers. According to an embodiment of the invention, suitable ionomers include, but are not necessarily limited to, ethylene-co-methacrylic acid copolymers (such as, for example, the film sold as Surlyn®, available from DuPont, Wilmington, Del.).

As the transdermal patch 2 releases the contents of drug 15, patch 2 may be replaced by a new patch 2. New patch 2 may then be employed for another drug delivery period. Alternatively, additional quantities of a substance or pharmaceutical agent may be inserted into patch 2 by appropriate means to effectively "re-load" the patch. In an embodiment, when patch 2 is replaced, it may be uncoupled from transducer assembly 18 or other source of the ultrasonic signal.

According to an embodiment of the invention, patch 2 is attached to one or more transducers 18 by a sonic adhesive or coupling agent. The sonic adhesive may be any suitable material, including, but not limited to, a mineral oil. An example of a suitable mineral oil is Draecol 9, available form Eastern Chemical, Philadelphia, Pa.

Alternatively, a fold at the top of transdermal patch 2 may be used to enable the transducer(s) 18 to slide into the topmost section of the patch, for example. Transducers 18 may be built directly into the structure of the patch as shown in FIG. 6.

Backbone 10 of patch 2 may be made from any suitable material, including, but not limited to, polyolefin film or polyvinyl chloride. An example of suitable materials are Polyvinyl Chloride Foam Tape 9772-L available from 3M, St. Paul, Minn. and Model Number 3M 9773 Foam Tape, a polyolefin foam tape with adhesive backing, available from 3M, St. Paul, Minn. Backbone material 10 may also possess adhesives, such as, for example, the pressure-sensitive acrylate adhesive used on 3M 9772-LFoam Tape, available from 3M, St. Paul, Minn., which will enable the patch 2 to adhere to the surface of the patient's skin.

According to an embodiment of the invention, backing member 10, comprising Model Number 9772-L Foam Tape (3M, St. Paul, Minn.) includes at least one aperture that is covered by sonic membrane 11 comprising Saran® film, Model Number Dow BLF-2014 (Dow chemical Co., Midland, Mich.) or Mylar® film, Model Number M34, DuPont Teijin Films, Wilmington, Del. At least one absorbent pad 14 comprising cellulose material (Model Number Vicell® #6009, Buckeye Absorbent Products, Memphis, Tenn.) may be placed such that ultrasonic energy is transmitted through sonic membrane 11 to absorbent pad 14. In the presence of an ultrasonic signal, insulin solution (Humulin®R, Eli Lilly, Indianapolis, Ind.) contained on or within absorbent pad 14 may move through semi-permeable membrane 13, comprising Surlyn® film (DuPont, Wilmington, Del.), and be delivered to a subject. Peel-away film 12 comprising UV-resistant anti-static polyethylene film (50 micrometer thickness) (Crystal-X Corp., Sharon Hill, Pa.) may be utilized.

According to an embodiment of the invention, patch 2 may enable ultrasonic signal transmission completely therethrough. Therefore, it may be desirable to minimize attenuation of the ultrasonic signal as it travels through the materials in patch 2. Of particular concern are pockets containing, for example, air, gas, or moisture located within the absorbent materials used in patch 2, which may act to later the frequency and/or intensity of the transmitted ultrasonic signal.

To facilitate an improved ultrasonic transmission through the patch, absorbent material may be treated using vacuum freeze drying to remove trapped air from within the absorbent material. In this method the material is frozen by freeze drying and then vacuum dried. One effect of freeze-drying is the reduction of the amount of trapped air within the weave of the absorbent material, thus making the absorbent material more resonance compatible with the frequency and intensity of the ultrasonic transmission and improving its attenuation properties.

According to an embodiment of the invention, the absorbent pad material may be soaked in an aqueous solution of 0.9% NaCl prior to the freeze-drying treatment. The pretreatment with the saline solution provides that a residue of NaCl remains in the absorbent material. The salt residue acts as a humectant, attracting water and thus maintaining some moisture within the absorbent pad. Preventing the absorbent pad from drying out allows the drug stored in the pad to remain in solution, preventing loss of moisture that may cause the drug solution to become increasingly concentrated. Concentration of the drug solution may be avoided, as it may lead to aggregation or precipitation of the active drug from the solution, impeding drug transport.

Suitable material for an absorbent pad may possess one or more of the following characteristics:

1) High absorbency for the selected drug presented in an emulsion or solution form.
2) The absorbent material is inert with respect to the select drug, or its excipient or preservatives used in the solution form of the drug, over a protracted period of storage time.
3) The absorbent material is resistant to degradation under exposure to ultrasound, and to releasing contaminants into the stored drug.
4) The absorbent material is essentially free of metallic, organic or inorganic contaminants.
5) The absorbent material is non-irritating to human skin and remains stable upon interaction with human sweat.
6) The absorbent material remains stable in a stored form for one year or more and is resistant to degradation with time when soaked with the drug.
7) The absorbent material may be composed of natural or synthetic materials.

According to an embodiment of the invention, the absorbent material is superabsorbent, defined as a material capable of absorbing about fourteen (14) or more times its weight in liquid Such a superabsorbent material provides the pad with the capacity to store the drug in a dilute solution or suspension This may be of particular importance for polypeptides such as insulin, which is believed to form multimeric structures when concentrated in solution. Preventing the absorbent pad from drying out, and thus maintaining insulin in dilute solution, maintains the insulin in monomeric form, which is most easily transported out of the patch and through the skin.

According to an embodiment of the invention, the absorbent material contains functional groups capable of cross-linking with the drug. Such cross-linking may act to stabilize the drug for storage while in patch 2. When an ultrasonic signal is applied through patch 2, upon reaching the absorbent material the ultrasonic signal may cause disruption of the cross-linking such that the drug is released from the absorbent material and is free to be delivered to the subject.

According to an embodiment of the invention, the absorbent material may be formed from material that contains moderate amount of crosslinking points, such that the absorbent material forms cross-linkages with the drug, but does not form cross-linkages that disrupt the native structure of the drug, and such that, upon exposure to ultrasonic signals, releases the cross-linking such that the drug is no longer bound to absorbent pad 14 and is free to be delivered to the tissue of the subject.

According to an embodiment of the invention, the absorbent material and the drug are cross-linked through hydrogen bonding. According to an embodiment of the invention, the absorbent material contains functional groups able to form hydrogen bonds with functional groups of a polypeptide drug, such as, for example, insulin. In this case, the hydrogen bonding acts to stabilize the structure of the drug. Upon exposure to an ultrasonic signals, the hydrogen bonding that cross-links the drug to the absorbent material is disrupted without breaking the hydrogen bonds that form the native secondary structure or other aspects of the structure of the polypeptide.

Table 1 lists at least some of the materials, which may be utilized in the construction of absorbent pad 14:

TABLE 1

EXAMPLE OF MATERIALS SUITABLE FOR ABSORBENT PAD 14

| | |
|---|---|
| Cellulose Fiber Pad | Cotton |
| Natural Sponge | Woven Cloth Fabrics |
| Polyurethane foams | Polyisocynurate Foams |
| Non-Woven Cloths | Fused Silica |
| Starch | Corn Meal |
| Wood Pulp fibers | Collagen Pads |
| Poly methyl methacrylate | Polyvinyl alcohol |
| Poly vinyl pyrrolidine | Poly acrylic acid |
| Poly (2-hydroxy ethyl methacrylate | Polyacrylamide |
| Poly ethylene glycol | Polylactides (PLA) |
| Polyglycolides (PGA) | Poly(lactide-Co-glycolides) |
| Polycarbonate | Chitosan |
| Poly (N-isopropylacrylamide) | |
| Co-Polymer formulations of Poly methacrylic acid and Poly ethylene glycol | |
| Co-Polymer formulations of Poly acrylic acid and Poly (N-isopropylacrylamide) | |
| Hyrdogels, e.g. Polyacrylamide, poly (propylene oxide Pluronic polyols family of gel materials, e.g. Pluronic-chitosan hydrogels | |
| Silica gels | |

Any other natural or synthetic materials, which may act to absorb the drug compound and be able to release the drug upon ultrasonic excitation.

According to an embodiment of the invention, the absorbent compound may be a non-woven material having a moderate amount of functional groups available for cross-linking. When the absorbent material contacts a drug, the functional groups of the absorbent material form cross-links with the drug such that the structure of the drug is stabilized in the absence of an ultrasonic signal. When an ultrasonic signal is transmitted through the patch to the absorbent material, the cross-linking may be disrupted such that the drug is released from the absorbent material without contamination of or disruption of the native structure of the drug.

According to an embodiment of the invention, the absorbent material is treated by freezing, followed by vacuum drying. Such freeze-drying of the absorbent material acts to reduce the amount of contaminants such as air or moisture that may be trapped in the absorbent material. Such contaminants may react with functional groups of the absorbent material, thus preventing these functional groups from forming cross-links with the drug. Upon freeze-drying, such contaminants are removed, thus freeing the cross-linking sites of the absorbent material such that the sites are free to form cross-linkages with the substance to be delivered. In addition, the freeze-drying may remove contaminants that otherwise might react with or contaminate the drug.

According to an embodiment of the invention, the absorbent material may be capable of retaining the drug in the absence of an ultrasonic signal, of releasing the drug upon excitation by an ultrasonic signal, and has absorbent properties such that any excess drug left upon the skin surface after the ultrasonic signal is terminated is reabsorbed into the absorbent pad and is not released until another ultrasonic signal is transmitted to the absorbent material. This function of the absorbent material enables the accurate control of the delivered drug dose by parameters of the ultrasonic signal and may eliminate the need for a semi-permeable "valving" membrane to control the dose. According to an aspect of the invention, a material having a capacity to absorb from between about one and about four times its weight in drug solution may provide the appropriate absorption/release/reabsorption properties that would enable controlled dosage release via ultrasound. The rate of absorption may be adjusted by utilizing different types and combinations of fibers to produce the absorbent material. For example, cellulose material may be produced from fibers originating from various types of wood (for example, "hard" versus "soft" woods) having different absorbent properties.

In accordance with an embodiment of the invention, as ultrasonic signals are transmitted through the patch 2 the signal massages the pores directly surrounding the hair follicle, increasing the permeability of the pore. Ultrasonic signals enhance the transport of drug 15 stored within absorbent pad 14 within patch 2, across semi-permeable membrane 13 and deposits drug 15 onto the skin surface, where drug 15 is absorbed into the body by traveling down the hair follicle to the hair root and into the vascular network.

In accordance with an embodiment of the invention, the ultrasonic transmission may have a frequency in the range of about 20 kHz to about 10 MHz. The intensity of said ultrasonic transmission may be in the range of about 0.01 W/cm$^2$ to about 5.0 W/cm$^2$. Changes in frequency and intensity levels may require alteration of the materials used in the construction of transdermal patch 2 to accommodate optimum performance in both drug delivery and in the valving function effected by semi-permeable film 13.

In accordance with an embodiment of the invention, while a waveform converting from sawtooth to square has been described, a traditional sinusoidal waveform may also be effective as a drug delivery waveform for the ultrasonic transmission.

Apparatus and methods according to the present invention are useful for delivering a wide variety of substances to a patient. As described in greater detail herein, the substances may be delivered, for example, transdermally, transcutaneously, intralumenally, and within solid tissue sites, where in all cases absorption of the substance or a pharmacologically active portion thereof into the underlying or surrounding tissue is phonophoretically enhanced by the application of ultrasonic or sonic energy. The substance may take any suitable form, including, but not limited to, liquids, gels, porous reservoirs, inserts, or the like, and the substance or pharmacologically active portion thereof may, for example, treat or alleviate an existing condition or prophylactically prevent or inhibit another condition of the patient. The effect of the substance may be local, such as providing for anti-tumor treatment, or may be systemic. Suitable medicaments include, but are not limited to, broad classes of compounds normally delivered through the skin and other body surfaces or into solid tissues.

In general, such medication may include or incorporate substances including, but not limited to, the following: anti-infectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimatics; xanthine derivatives; cardiovascular preparations including, but not limited to, potassium and calcium channel blockers, beta-blockers, and antiarrhythmics; antihypertensives; diuretics; vasodilators including general coronary, peripheral and cerebral; central nervous system stimulants; cough and cold preparations, including decongestants; hormones, including, but not limited to steroids, including, without limitation, estradiol, and corticosteroids; hypnotics; immunosuppressives; muscle relaxants; parasympatholyttics; psychostimulants; sedatives; and tranquilizers. By the method of the present invention, ionized and nonionized drugs may be delivered, as can drugs of high or low molecular weight.

Proteinaceous and polypeptide drugs represent one class of drugs suitable for use in conjunction with the presently disclosed invention. Such drugs cannot generally be administered orally in that they are often destroyed in the gastrointestinal tract or metabolized in the liver. Further, due to the high molecular weight of most polypeptide drugs, conventional transdermal delivery systems are not generally effective.

Common examples of pharmaceutical or nutritional compounds which may be contained within transdermal patch 2 of this invention include, but are not limited to: acetaminophen, antibiotics, aspirin, corticosterone, erythromycin, ibuprofen, insulin, nitroglycerin, nicotine, steroids, including without limitation, progesterones, estrogens, for example, estradiol, and vitamins. Suitable forms of insulin include, but are not necessarily limited to, Humulin ®R and Humulog®, both available from Eli Lilly and Company, Indianapolis, Ind. Any other substance, including, but not limited to, pharmaceutical and/or nutritional compounds used for nutraceutical, medicinal or pharmaceutical purposes, and any combinations thereof, may also be utilized. It may also desirable to use the method of the invention in conjunction with drugs to which the permeability of the skin is relatively low, or which give rise to a long lag-time. Application of ultrasonic signals as described herein has been found to significantly reduce the lag-time involved with the transdermal administration of most drugs.

The use of ultrasonic signals coupled with iontophoresis, the application of electric currents applied to the skin, has been attempted in various forms of drug delivery. In some instances ultrasonic signals was used together with iontophoresis while in others ultrasound was a pre-treatment to the application of iontophoresis. Applicants have noted the method of iontophoresis in combination with the apparatus of this invention can be used to enhance molecular transport through the skin.

The use of chemical substances, often referred to as chemical enhancers, can enhance drug transport in this invention as well.

According to an embodiment of the invention, a safety feature, which indicates that the patch is empty or has been used, may be incorporated. The use of a ultrasonic contrast agent or color forming label within the patch which will turn color, for example from green to red, when exposed to ultrasound, may be provided as a means of indicating that the patch has been used.

According to an embodiment of the present invention, transdermal patch 2 may be fitted with a bio-sensor which detects the glucose level of the patient, either through invasive or non-invasive means, with the data from the sensor being used to control the application of medication from the patch and the timing of the drug delivery.

According to an embodiment of the invention, transdermal patch 2 may be fitted with a bio-sensor, which would detect the amount of medication actually delivered to the patient. Such a sensor may measure the electrical resistance of the patient's skin. Delivery of a drug through the skin causes a readable change in the electrical conductivity of the skin tissue surrounding the transport site. The data from such a bio-sensor could be used to record the actual quantity of the drug delivered from the patch to the patient.

Having described the invention in the above detail, those skilled in the art will recognize that there are a number of variations to the design and functionality for the device, but such variations of the design and functionality are intended to fall within the present disclosure. Further, although the invention has been disclosed with a certain degree of particularity, it is understood that the present disclosure of the preferred forms has been made by way of example, and that numerous changes in the details of construction and combination and arrangement of parts and steps may be made without departing from the spirit and scope of the invention as hereinafter claimed.

What is claimed is:

1. A system being suitable for being secured substantially adjacent to a surface of a subject so as to effect delivery of at least one substance through said surface and into said subject responsively to a sonic applicator being positioned proximate thereto and generating at least one sonic transmission, comprising:

a substantially planar backing sheet having at least one aperture that receives the at least one sonic transmission, said at least one substance being releasably secured substantially adjacent to said at least one aperture; and, a sonic membrane disposed across said at least one aperture and between the sonic applicator and at least one substance, so as to communicate said at least one sonic transmission to said at least one substance and effect said delivery of said at least one substance through said surface of said subject.

2. The system of claim 1, further comprising:

a pad releasably securing said at least one substance substantially adjacent to said at least one aperture.

3. The system of claim 2, further comprising a patch, distinct from the sonic applicator and comprising the backing sheet, sonic membrane and pad.

4. The system of claim 3, wherein the patch further comprises a sonically activated semi-permeable membrane substantially adjacent to the pad and that provides a sonically activated valving function.

* * * * *